United States Patent

Melyon

[11] Patent Number: 5,597,482
[45] Date of Patent: Jan. 28, 1997

[54] WATER PURIFICATION APPARATUS

[76] Inventor: Solly Melyon, 7834 Bankside Dr., Houston, Tex. 77071

[21] Appl. No.: 428,372

[22] Filed: Apr. 25, 1995

[51] Int. Cl.$^6$ ............................ C02F 1/32; B01D 27/08
[52] U.S. Cl. ................... 210/209; 210/232; 210/256; 210/260; 422/186.3
[58] Field of Search ....................... 210/192, 198.1, 210/205, 209, 232, 256, 260, 748; 422/186.3, 906

[56] References Cited

U.S. PATENT DOCUMENTS

| | | | |
|---|---|---|---|
| 4,719,012 | 1/1988 | Groezinger et al. | 210/232 |
| 4,762,613 | 8/1988 | Snowball | 210/192 |
| 4,766,321 | 8/1988 | Lew et al. | 422/186.3 |
| 4,857,204 | 8/1989 | Joklik | 422/186.3 |
| 4,909,931 | 3/1990 | Bibl | 210/192 |
| 4,968,489 | 11/1990 | Peterson | 422/186.3 |
| 4,971,687 | 11/1990 | Anderson | 210/256 |
| 5,178,758 | 1/1993 | Hwang | 210/205 |
| 5,266,215 | 11/1993 | Engelhard | 210/192 |
| 5,290,439 | 3/1994 | Buchwald | 210/748 |

*Primary Examiner*—Peter A. Hruskoci
*Assistant Examiner*—Theodore M. Green
*Attorney, Agent, or Firm*—Bill B. Berryhill

[57] ABSTRACT

Water purification apparatus provides an elongate ultraviolet lamp extending into a surrounding hollow tube capable of passing ultraviolet light. The lamp and tube are surrounded by a housing, with water inlet and outlet, which provides an annular flow path around the hollow tube through which water may pass for exposure to ultraviolet light. An ultraviolet reflective surface in the annular flow path reflects ultraviolet rays through the water. A unique seal is provided around an open end of the hollow tube to seal the lamp from water in the housing.

25 Claims, 1 Drawing Sheet

WATER PURIFICATION APPARATUS

BACKGROUND OF THE INVENTION

1. Field of the Invention

The present invention pertains to water treatment and water purification. More specifically, the present invention pertains to apparatus for filtering and/or ultraviolet treatment of water flowing from a water supply.

2. Description of the Prior Art

Most sources of water are contaminated to varying degrees. In an attempt to remove some of these contaminants, various methods and apparatus have been developed over time. Small suspended particles in water may be removed by mechanical filtration. Other types of filters, such as activated carbon may be utilized to remove other impurities which affect taste, odor, color, chemical composition, etc. Ultraviolet light (U.V.) has been used to destroy viruses and bacteria in water.

In commercial applications, where water is filtered and treated with U.V. rays, filtration and U.V. purification are performed in separate apparatus. After filtering, the water may flow through a stainless steel chamber in which an ultraviolet lamp has been inserted. The water flows into the chamber, around the U.V. lamp and out of the chamber. The stainless steel chamber is typically cylindrical and its inner surface is polished to reflect U.V. rays from the U.V. lamp to enhance or increase the effectiveness thereof. Such stainless steel chambers are relatively expensive.

In recent years, combination water filters and sterilizers have been developed which utilize mechanical and carbon filtering in combination with ultraviolet sterilization of water in a composite unit. Such units, developed primarily for household uses, may be connected to a residential water tap and supplied with power for an ultraviolet lamp by ordinary 120 volt A.C. current. Examples of such combination water filter and sterilizers may be seen in U.S. Pat. Nos. 3,551,091 and 4,971,687.

In such combination water filter and sterilizers, a typical off-the-shelf annular filter surrounds a quartz tube into which is inserted an elongated ultraviolet lamp. The outer surface of the quartz tube and the inner surface of the annular filter define an annular passageway through which water passes, after filtration by the filter means, for exposure to ultraviolet rays emanating from the ultraviolet lamp. In U.S. Pat. No. 4,971,687 an elongated teflon or other transparent material tube is provided between the annular filter and the quartz tube surrounding the ultraviolet lamp to assure maximum time of exposure of the water to ultraviolet rays before exiting the unit. While such an arrangement may enhance ultraviolet light sterilization of the water, it also complicates the manufacturing of such a unit and increases the cost thereof. Other off-the-shelf filters are provided with inner and outer liners, between which filter materials are disposed, which direct the flow of water from one end of the filter to the other prior to exposure to U.V. treatment.

One of the major problems associated with combination and filter and sterilization units such as those just described is in sealing around the tube which surrounds the ultraviolet lamp. The tube must of necessity be opened at one end so that the ultra-violent lamp may be inserted thereinto. The open end must then be sealed, usually in a head or base unit to which it is attached, so that no water leaks past this connection for possible exposure to electrical components which provide power for the ultraviolet lamp. Most units of the prior art provide an O-ring seal around the open end of the hollow tube which frequently does not satisfactorily seal against household water pressure which may exceed 90 psi.

Thus, while a number of fairly satisfactory combination filter and sterilization units have been developed, the search continues for such units which are safe, efficient, cheap, easy to maintain and of improved ability to filter and purify water.

SUMMARY OF THE PRESENT INVENTION

The present invention provides water filtering and purification apparatus which includes an electrical module having a socket connectable to a source of electricity and upwardly from which may extend an elongated ultraviolet light ray emitting lamp. The unit is provided with an elongated housing for surrounding the lamp. The housing may be provided with a base having a water inlet and a water outlet and which is provided with a central opening through which the lamp may be inserted for extension into the housing. A hollow transparent elongate tube, capable of passing ultraviolet rays and closed at one end and open at the other, may be attached to the housing base for fluidtight connection therewith. The exterior of the elongate tube defines the inner wall of an annular passage through which water flowing from the housing inlet to the housing outlet may flow while being exposed to ultraviolet rays from the lamp.

In a preferred embodiment of the invention a thin sheet of ultraviolet ray reflective material, such as stainless steel, is insertable into the annular passage to reflect ultraviolet rays passing through the water in the annular flow path. Thus sterilization of the water is further enhanced by reflecting ultraviolet rays back into the water.

In a preferred embodiment of the invention, a unique seal is provided in the central opening of the housing base for surrounding the opened end of the hollow tube in a fluidtight connection. The seal may include an annular elastomeric member insertable into a counterbore of the central opening and engageable by a pressure plate by which an axial force may be applied thereto to radially expand the seal outwardly against the central opening and inwardly against the hollow tube to provide the fluidtight connection. In a preferred embodiment of the invention, the hollow tube has a radial flange therearound and the elastomeric member is provided with an internal annular groove for sealingly receiving the radial flange.

Thus, the water filtering and purification apparatus of the present invention provides filtering and enhanced ultraviolet ray purification of water in a single combination unit. Furthermore, it provides for fluidtight sealing which is far superior to the prior art. These features are provided in a simple and cost effective unit. It is economically manufactured and especially effective in removing contaminants which affect the taste, odor, color and chemical composition of water and in destroying viruses and bacteria which may be contained therein. Many other objects and advantages of the invention will be appreciated when reading the specification which follows in conjunction with accompanying drawing.

DESCRIPTION OF A PREFERRED EMBODIMENT

Figure 1:
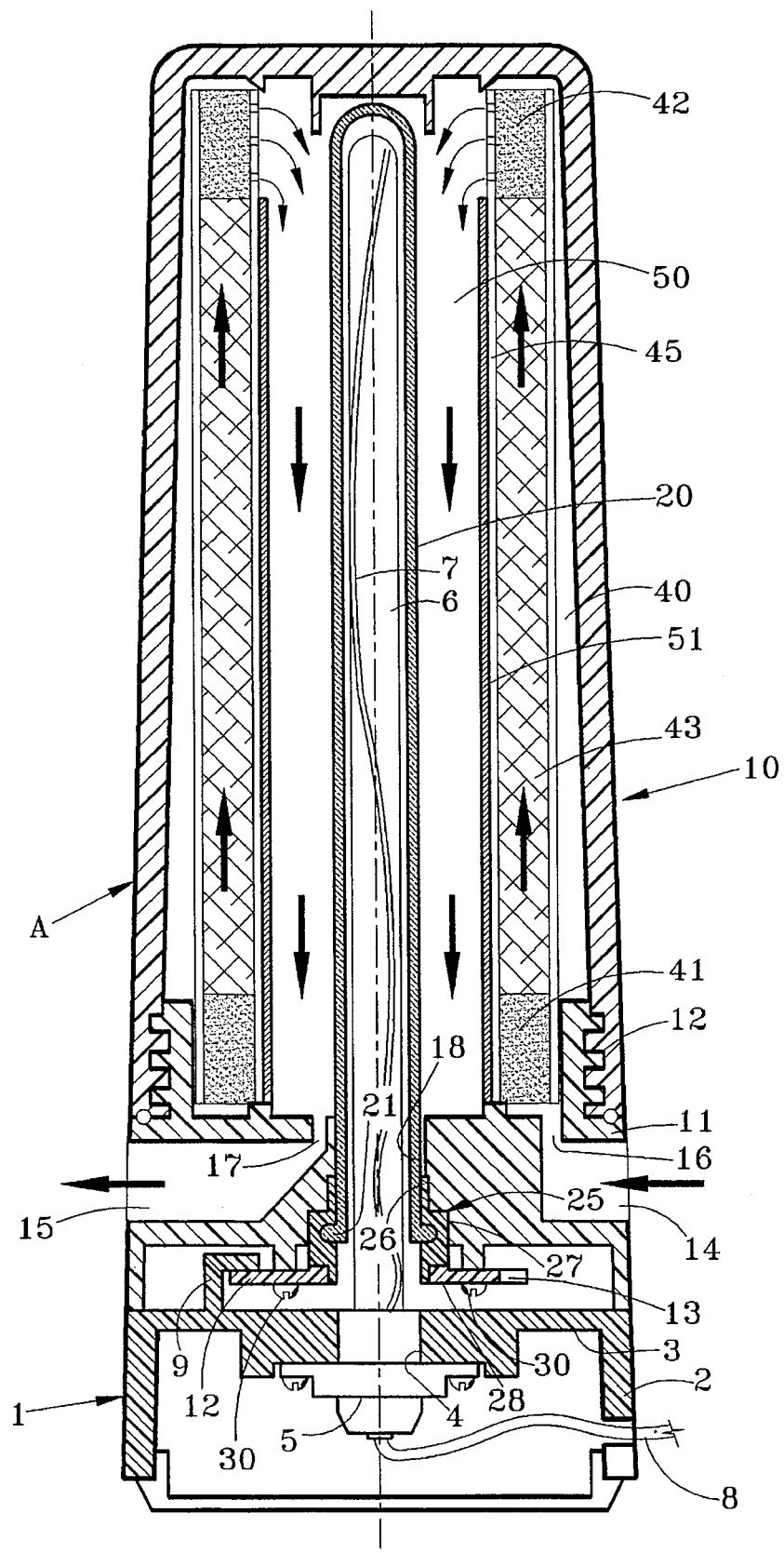
FIG. 1 is an elevation view, partially in section, of water filtering and purification apparatus of the present invention, according to a preferred embodiment thereof.

Referring to FIG. 1, there is shown water filtering and treatment apparatus A which includes an electrical module 1 on which the entire unit may be supported. The electrical module 1 may be formed with a cylindrical or tapered skirt 2 and an upper, circular plate 3 in which is provided a central opening 4. Mounted in the central opening 4, in any suitable fashion, is an electrical socket 5 for receiving the base of an elongated ultraviolet lamp 6 having a filament 7 therein. This socket 5 may be connected by an electrical cord 8 to a source of electrical power, e.g. 120 volt A.C. current.

Surmounted on the electrical module 1 is an elongate hollow housing 10 connected to a housing base 11. The base 11 and housing 10 may be provided with cooperating threads for a threaded connection 10a. This allows the housing 10 to be removed, if desired. The base 11 is also removably attached to the electrical module 1. This may be accomplished in several ways. In the exemplary embodiment, a plurality of lugs 9 provided on the electrical module 1 may be engaged by the edges of a plate 12 which is attached to the housing base 11 as will be more fully understood hereafter. The plate 12 may be provided with an equal number of slots 13 which, when the base is twisted or rotated less than forty-five degrees, are alignable with the lugs 9 to allow the housing base 11 to be removed. Removal of the housing base 11 allows replacement of the ultraviolet lamp 6.

The base 11 has a water inlet 14 and a water outlet 15. The water inlet 14 communicates with the outer interior of the housing 10 through port 16 and the water outlet 15 communicates with the inner housing interior through one or more ports 17. The housing base 11 is also provided with a central opening 18 through which the lamp 6 may be inserted for insertion into the housing 10.

Surrounding the lamp 6 is a hollow elongate tube 20 of a material, such as quartz, which is transparent to ultraviolet rays emanating from lamp 6. The tube 20, which is also insertable through base opening 18, is closed at its upper end and opened at the lower end to permit insertion of the lamp 6 thereinto. In a preferred embodiment, the tube 20 is provided around the open end thereof with a radial flange lip, or bead 21.

It is important that the opened end of the hollow tube 20 be secured to the housing base 11 in a fluidtight seal. This is accomplished, in the exemplary embodiment with an elastomeric seal 25 having a cylindrical interior which is provided with an annular groove for sealingly receiving the radial flange, lip or bead 21 of the hollow tube 20. The exterior of the elastomeric seal 25 has a small diameter portion 26 which surrounds the hollow tube 20 immediately above the radial flange 21 and a large diameter portion 27 which sealingly engages a counterbore of the central opening 18. Another small diameter exterior portion 28 of the elastomeric seal may engage a central opening of pressure plate 12. The pressure plate 12 is attached to the underside of the base 11 by a plurality of screws 30, which when tightened, cause the pressure plate 12 to apply an axial force to the seal member 25, radially expanding the seal member 25 against the central opening 18 and its counterbores and inwardly against the hollow tube 20, particularly the flange 21 thereof, to provide a secure fluidtight seal capable of withstanding household water pressure in excess of 90 psi.

Carried within the housing 10, concentrically surrounding the hollow tube 20, is an annular filter element 40. The filter element 40 can be made in a number of ways and is readily available off-the-shelf in today's market. The filter assembly 40, as shown in the drawing, includes a lower annular or donut shaped mechanical sediment filter 41, and an upper annular shaped or donut shaped mechanical micron filter 42 between which may be provided activated carbon 43. These filter sections 41, 42, 43, may be outwardly and inwardly defined by outer cylindrical wall 44 and inner cylindrical wall 45. The lower filter element 41 is perforated in such a way that water flowing inwardly through the inlet port 14 and port 16 will pass through the filter 41 upwardly through the activated carbon 43 and the upper filter element 42. Filter element 42 is perforated in such a way as to allow the water to then exit into an annular passage 50 outwardly defined by the cylindrical wall 45 and inwardly defined by the outer surface of the hollow tube 20. The water eventually exits through port 17 and outlet 15. As it passes through the annular passage 50 the water is purified by the ultraviolet rays being emitted form the lamp 6 and transmitted through the hollow tube 20.

In a preferred embodiment of the invention, the outer wall of the annular passage 50, i.e. the inner wall 45 of the filter assembly 40, is preferably lined with a material 51 which reflects ultraviolet rays passing through the water in the annular passage 50. In a preferred embodiment this material is stainless steel. The stainless steel liner 51 may be conveniently formed of a rectangular piece of tempered stainless steel shim stock the length of which is substantially equal to the length of the annular flow passage 50 and the width of which is substantially equal to the outer perimeter of the flow passage 50. This shim stock, e.g. three thousandths of an inch in thickness, may be deflected or rolled into the shape of a thin cylinder or sleeve and inserted into the interior of the filter assembly 40 prior to its assembly in the unit. So rolled, the shim stock is outwardly biased to lie closely against the inner wall 45. Thus the water passing through the annular passage 50 is exposed to ultraviolet rays emanating from the lamp 6 and again exposed to ultraviolet rays being reflected from the stainless steel liner 51. Obviously, this enhances the purification of the water by double ultraviolet ray exposure and increased destruction of harmful living organisms, viruses and bacteria in the water. Furthermore, the stainless steel liner 51 protects the material of cylindrical wall 45 from exposure to U.V. rays. If not so protected, the cylindrical wall 45 may, as with prior art, disintegrate from U.V. exposure, resulting in potential water contaminants therefrom.

The water purification apparatus of the present invention is assembled in the following manner. An ultraviolet lamp 6 is inserted into the socket 5 of the electrical module 1 so that the ultraviolet lamp 6 extends upwardly therefrom. Then the hollow tube 20 with the elastomeric seal 25 is inserted through the central opening 18 of the housing base 11 while the housing base 11 is separated from both the electrical module 1 and the housing 10. The seal 25 is placed in proper disposition within the counterbores of the central opening 18. The pressure plate 12 is then attached to the underside of the housing base 11 with the screws 30 applying an axial pressure to the elastomeric seal 25 and creating a fluidtight seal between the housing base 11 and the hollow tube 20. At this point, the housing base 11 may be placed on the electrical module 1 as the lamp 6 is inserted into the hollow tube 20. The housing base 11 may be rotated so that the pressure plate 12 properly engages the attachment lugs 9 of the electrical module 1. Next the annular filter unit 40 may be placed on the housing base 11. Finally, the housing 10 may be placed around the filter assembly 40 and the hollow tube 20 and attached to the housing base 11 by threads 12.

In operation, the water inlet 14 may be connected to a source of water and the outlet 15 connected to a point of use. Water enters through the water inlet 14 and port 16 through filter sections 41, 43 and 42, exiting the filter assembly 40 and entering the annular passage 50 where the filtered water is purified by exposure to ultraviolet rays emitted from the lamp 6. As previously discussed, these rays are also reflected by the stainless steel liner 51 to enhance purification. Finally the filtered and purified water exits port 17 and water outlet 15 for eventual use.

Thus, the water filtering and purification apparatus of the present invention provides a combination unit which filters and purifies water in a straight-forward unique combination. Purification is enhanced over methods of the prior art by providing reflective surfaces so that ultraviolet rays pass through water and are reflected therethrough. These reflective surfaces may be provided by a sheet of stainless steel which may be simply and cheaply rolled into a cylinder and inserted into the interior of an off-the-shelf annular filter unit.

The apparatus of the present invention is provided with a seal which is much superior to those of the prior art. The seal surrounds the opening of a tube in which an ultraviolet lamp is inserted to assure that water does not contact the lamp or other electrical components associated therewith.

While a single embodiment of the invention has been described herein, many variations thereof can be made without departing from the spirit of the invention. Accordingly, it is intended that the scope of the invention be limited only by the claims which follow.

I claim:

1. Water purification apparatus comprising in combination:

an electrical module having a socket connectable to a source of electricity and upwardly from which extend an elongated ultraviolet light ray emitting lamp;

an elongate housing attachable to said electrical module for surrounding said lamp and having a water inlet and a water outlet;

a hollow elongate tube centrally disposed in said housing, capable of passing ultraviolet rays, closed at one end and opened at the other to permit insertion of said lamp thereinto;

an outer annular passage defined by inner and outer cylindrical walls between which is provided filter means, said outer annular passage providing a flow path for water flowing from said housing inlet and said filter means providing filtering of suspended particles from said water prior to exposure to ultraviolet rays from said ultraviolet light;

an inner annular passage the inner surface of which is defined by the exterior of said elongate tube and the outer surface of which is defined by said inner cylindrical wall of said outer annular passage spaced therefrom, said inner annular passage providing a second flow path, counter to the flow of said first mentioned flow path, for water flowing through said outer annular passage from said housing inlet for continuous flow to said housing outlet and exposing said water to ultraviolet light rays from said lamp; and a thin sheet of ultraviolet ray reflective material lining said inner cylindrical wall to block ultraviolet rays from said first flow path and to reflect ultraviolet rays passing through said second flow path.

2. Water purification apparatus as set forth in claim 1 in which said sheet of ultraviolet ray reflective material comprises a sheet of tempered stainless steel shim stock which may be deflected into a cylindrical sleeve and inserted into said inner annular passage, being outwardly biased into close contact with said inner cylindrical wall.

3. Water purification apparatus as set forth in claim 1 in which said sheet of ultraviolet ray reflective material comprises a sheet of stainless steel which may be deflected into a cylindrical sleeve and inserted into said inner annular passage.

4. Water purification apparatus as set forth in claim 3 in which said sheet of stainless steel, prior to deflection thereof, is of a length substantially the same as the length of said inner annular passage and of a width substantially equal to the outer perimeter of said inner annular passage.

5. Water purification apparatus as set forth in claim 1 in which said housing is provided with a base which is connected to said electrical module and having a central opening in a fluidtight connection with the open end of said hollow elongate tube preventing water from contacting said lamp or the electrical module from which it extends.

6. Water purification apparatus as set forth in claim 5 including seal means disposed in said central opening surrounding the open end of said hollow tube, said seal means being an annular elastomeric member insertable into a counterbore of said central opening and engaged by a pressure plate by which an axial force may be applied thereto to radially expand outwardly against said central opening and inwardly against said hollow tube to provide said fluidtight connection.

7. Water purification apparatus as set forth in claim 6 in which the open end of said hollow tube has a radial flange therearound, said elastomeric member being provided with an internal annular groove engageable by said radial flange.

8. Water purification apparatus as set forth in claim 7 in which said elastomeric seal comprises a cylindrical interior in which is provided said annular groove, the exterior of said seal being defined by a small diameter portion, surrounding a portion of said hollow tube adjacent said radial flange and sealingly engaging said central opening, and an adjacent large diameter portion sealingly engaging said central opening counterbore.

9. Water purification apparatus as set forth in claim 8 in which said elastomeric seal has another small diameter portion adjacent said large diameter portion for sealingly engaging an opening in said pressure plate.

10. Water purification apparatus as set forth in claim 1 in which said housing and said electrical module are connected by cooperating connection means which, upon rotation of said housing by less than forty-five degrees, allows said housing and said elongate tube to be separated from said electrical module for replacement of said ultraviolet light ray emitting lamp.

11. Water purification apparatus as set forth in claim 10 in which said connection means comprises a plate connected to one of said housing and said electrical module having a plurality of slots radially disposed therein and a plurality of lugs projecting from the other of said housing and said electrical module, said lugs being alignable with said slots upon said rotation of said housing to allow said separation of said housing and said tube from said electrical module.

12. Water purification apparatus comprising in combination:

an electrical module having a socket connectable to a source of electricity and upwardly from which extends an elongated ultraviolet light ray emitting lamp;

an elongated housing having a base attachable to said electrical module having a water inlet and a water outlet and being provided with a central opening through which said lamp may be inserted for extension into said housing;

a hollow elongate tube, surrounded by said housing, capable of passing ultraviolet light rays, closed at one end and opened at the other, said opened end being attached to said housing base in fluidtight connection therewith surrounding said lamp to isolate said lamp from the area of said housing surrounding said hollow tube, water flowing from said water inlet, through said area surrounding said hollow tube to said water outlet while being exposed to ultraviolet light rays from said lamp; and seal means disposed in said central opening of said housing base and surrounding said opened end of said hollow tube, said seal means being an annular elastomeric member insertable into a counterbore of said central opening and engageable by a pressure plate by which an axial force may be applied thereto to radially expand outwardly against said central opening and inwardly against said hollow tube to provide said fluidtight connection.

13. Water purification apparatus as set forth in claim 12 in which the opened end of said hollow tube has a radial flange therearound, said elastomeric member having an internal annular groove for sealingly receiving said radial flange.

14. Water purification apparatus as set forth in claim 13 in which said elastomeric member has a cylindrical interior in which said annular groove is provided, the exterior of said elastomeric member having a small diameter portion surrounding said hollow tube immediately adjacent said radial flange thereof and a large diameter portion sealingly engaging said central opening counterbore.

15. Water purification apparatus as set forth in claim 12 including annular filter means carried in said housing and surrounding said hollow tube but outwardly spaced therefrom to provide an annular passageway through which water passing from said water inlet and through said filter means may pass before exiting said water outlet for exposure to ultraviolet light rays being emitted from said lamp.

16. Water purification apparatus as set forth in claim 15 in which the outer wall of said annular passage is defined by a cylindrical surface which forms the inner wall of said annular filter means.

17. Water purification apparatus as set forth in claim 16 in which said outer wall of said annular passage is lined with a material which reflects ultraviolet rays passing through said water from said lamp.

18. Water purification apparatus as set forth in claim 17 in which said reflective material is stainless steel.

19. Water purification apparatus as set forth in claim 18 in which said stainless steel is a thin sheet of tempered stainless steel shim stock which may be deflected into a tube and inserted into said annular filter means to lie adjacent said inner wall thereof, said stainless steel shim stock being outwardly biased to hold itself in position against said cylindrical surface.

20. Water purification apparatus as set forth in claim 12 in which said housing and said electrical module are connected by cooperating connection means which, upon rotation of said housing by less than forty-five degrees, allows said housing and said elongate tube to be separated from said electrical module for replacement of said ultraviolet light ray emitting lamp.

21. Water purification apparatus as set forth in claim 20 in which said connection means comprises a plate connected to one of said housing and said electrical module having a plurality of slots radially disposed therein and a plurality of lugs projecting from the other of said housing and said electrical module, said lugs being alignable with said slots upon said rotation of said housing to allow said separation of said housing and said tube from said electrical module.

22. Filter apparatus for use in water purification apparatus of the type having an electrical module from which extends an elongated ultraviolet lamp and having a housing in which is centrally disposed an elongated tube, capable of passing ultraviolet rays and into which said ultraviolet lamp may be inserted, said housing having a water inlet and a water outlet, said filter apparatus, being placeable around said tube, comprising an inner cylindrical wall, an outer cylindrical wall and an annular space therebetween in which is provided filter material, said inner cylindrical wall and the outer surface of said elongated tube forming an annular passageway through which water passing from said water inlet and through said filter material is directed prior to exiting through said water outlet for exposure to ultraviolet light rays from said ultraviolet lamp characterized by a thin sheet of ultraviolet ray reflective material disposed against said inner cylindrical wall to block ultraviolet rays from said filter apparatus and to reflect ultraviolet rays passing through said water in said annular passageway.

23. Filter apparatus as set forth in claim 22 in which said sheet of ultraviolet ray reflective material comprises a sheet of stainless steel which may be deflected into a cylindrical sleeve and inserted into said filter apparatus.

24. Filter apparatus as set forth in claim 23 in which said sheet of stainless steel is a sheet of tempered shim stock which when deflected into said cylindrical sleeve and inserted into said filter apparatus is self-biasing in an outward direction for close contact with said inner cylindrical wall.

25. Filter apparatus as set forth in claim 23 in which said sheet of stainless steel, prior to deflection thereof, is of a length substantially the same length as said annular passageway and of a width substantially equal to the outer perimeter thereof.

* * * * *